Nov. 5, 1957 M. ELLIOTT Plant Pat. 1,656
CARNATION PLANT
Filed Feb. 9, 1955
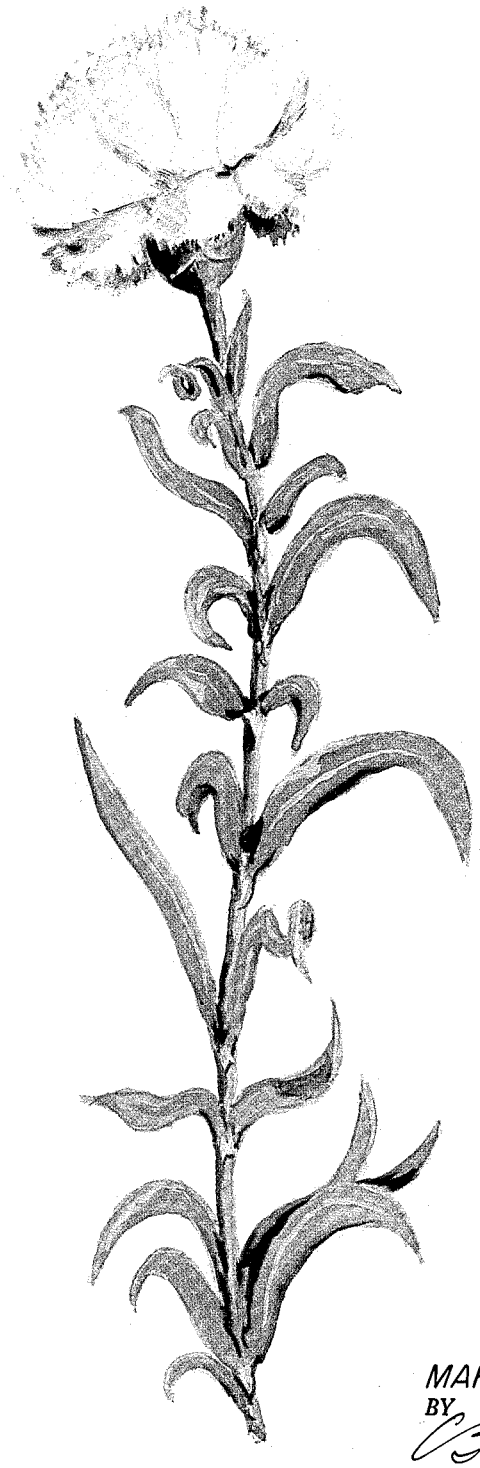
INVENTOR.
MARION ELLIOTT
BY C. B. Messenger
ATTORNEY United States Patent Office Plant Pat. 1,656
Patented Nov. 5, 1957

1,656

CARNATION PLANT

Marion Elliott, Denver, Colo.

Application February 9, 1955, Serial No. 487,233

1 Claim. (Cl. 47—60)

The present invention relates to an improved variety of carnation plant and, more particularly, to such an improved variety developed from the previously existing William Sim, red and Miller's Yellow varieties.

In development of the new and improved variety, the main objectives have been to provide carnations that would be well suited to commercial greenhouse culture and that would in general meet more restrictive grading standards.

These general objectives and others of singular importance have been attained by the flower herein disclosed, the main characteristics of which are shown in the accompanying drawing.

The characteristic color of the plant may be identified by reference to color plates listed in "A Dictionary of Color" by A. Maerz and M. Rea Paul, copyright 1950. The color of the major portion of the blossom closely corresponds to the color Oyster (White)+ as shown on Plate 10 at B–1 but is of a slightly purer white than indicated by such plate, while the center of the blossom corresponds to the reference color Marguerite Yellow, Plate 10 at C–1.

Before detailed study of plant characteristics, however, the steps followed to produce this new variety will be discussed. In general, the new variety is derived from the previously existing varieties known as the William Sim, red, Plant Patent No. 669, and Miller's Yellow, an unpatented variety. As a first step, the male William Sim, red, variety was crossed on to the Miller's Yellow to produce seed. One seed from that derived above produced a plant single (having only five petals), the pollen from which was introduced on to an original William Sim, red variety as the female. The product of this cross included several pink singles and one plant of the new improved variety. Cuttings from this one plant have produced a considerable number of plants and flowers. These subsequent plants have all been true to type and have uniform characteristics indicating a true improved variety.

Having observed production of the new variety and the William Sim, red variety in side-by-side relation under identical conditions, comparative analysis is possible. Such analysis indicates the improved nature of the new strain and also serves to point out the true characteristics of this type plant.

By comparison the new variety is found to have a larger ball-shaped flower having a higher crown and a more uniform color than that of the William Sim, white, a sport variety of the William Sim, red variety. The flower has a stronger, more penetrating, but characteristic fragrance, and the outer series of petals on the flower is observed to be broader, longer and more deeply serrated with a tendency to spread outwardly giving the flower its ball shape.

The fuller shape of the flower is perhaps in part due to the shorter and thicker calyx which in itself has proved to be sturdier and, consequently, more resistant to splitting even in periods of heaviest production. From a marketing standpoint this characteristic is of considerable importance.

Under identical conditions of cultivation the new variety has relatively broader plant leaves and a stronger stem than the William Sim varieties. The leaves seem to curl more readily, and the strong stem makes longer stems possible. With long stems and a fuller flower, the new variety weighs more than the William Sim varieties and easily meets even the more rigid grading standards.

Another characteristic enhancing the value of the new variety is a tendency to produce prolific cuttings which may be used to start new plants. Further, the cuttings are generally located at the lower nodes on the stem, so that a long stem flower may be produced without sacrifice of cuttings.

The new improved variety has been reproduced in quantity in commercial greenhouses at Adams City, Colorado, by breaking cuttings away from their point of occurrence at the nodes on the plant stems and cultivating said cuttings in a water solution until a root system is formed. Subsequently, the rooted cuttings are planted in well fertilized bench soil for production of additional blossoms and more cuttings.

While showing general improvement in all the above characteristics without impairment of its resistance to disease and insects, the new variety has yet another important characteristic that in part explains and emphasizes all its improved features. The new variety actually has more petals in the flower than the parent William Sim varieties. By average count the new variety has seventy petals in the flower as compared to sixty petals for the William Sim varieties.

Having more petals and characteristically larger petals in the outer positions, the fuller shape, the heavier weight and, consequently, the better grading of the flower are assured.

Having described the characteristics of a new variety of plant, the following claim is entered:

A new and distinct variety of carnation plant substantially as herein shown and described characterized as to novelty and usefulness—as compared to the parent William Sim, red variety—by a shorter calyx resistant to splitting, and a fuller flower having a greater number of petals, larger outside petals and stronger fragrance, combined with more vigorous, prolific and healthier habit of growth of plant flower and foliage especially under commercial greenhouse conditions.

No references cited.